United States Patent
Boulanger et al.

(10) Patent No.: US 12,290,636 B2
(45) Date of Patent: May 6, 2025

(54) RESPIRATORY DEVICES

(71) Applicant: Speed to Market LTD., Hong Kong (CN)

(72) Inventors: Dave Boulanger, Hong Kong (CN); Bob Zhang, Shenzhen (CN); Colin Gallacher, San Diego, CA (US); Yi Ding, Montreal (CA); Felix Desourdy, Montreal (CA)

(73) Assignee: NORTHMAN IP HOLDCO LIMITED, Hong Kong (CN)

( * ) Notice: Subject to any disclaimer, the term of this patent is extended or adjusted under 35 U.S.C. 154(b) by 902 days.

(21) Appl. No.: 17/477,595

(22) Filed: Sep. 17, 2021

(65) Prior Publication Data

US 2022/0401686 A1 Dec. 22, 2022

Related U.S. Application Data

(60) Provisional application No. 63/211,237, filed on Jun. 16, 2021.

(51) Int. Cl.
*A61M 16/12* (2006.01)
*A61M 16/00* (2006.01)
(Continued)

(52) U.S. Cl.
CPC ...... *A61M 16/101* (2014.02); *A61M 16/0063* (2014.02); *A61M 16/0066* (2013.01); *A61M 16/12* (2013.01); *A61M 16/209* (2014.02)

(58) Field of Classification Search
CPC ............ A61M 16/101; A61M 16/0063; A61M 16/209; A61M 16/0066; A61M 16/12;
(Continued)

(56) References Cited

U.S. PATENT DOCUMENTS 4,822,384 A 4/1989 Kato et al.
4,838,257 A 6/1989 Hatch
(Continued)

FOREIGN PATENT DOCUMENTS

CN 106456927 A 1/2011
CN 111821552 A 10/2020
(Continued)

OTHER PUBLICATIONS

National Intellectual Property Administration PRC; International Search Report of the International Search Authority for PCT/IB2022/055208 (common priority claim as the present application); Sep. 21, 2022; 5 pages.
(Continued)

*Primary Examiner* — Timothy A Stanis
*Assistant Examiner* — Tyler A Raubenstraw
(74) *Attorney, Agent, or Firm* — Black McCuskey

(57) ABSTRACT

A respiratory device can include an oxygen generator and a ventilator. The oxygen generator can include a first inlet to ambient air, a vacuum or pressure swing oxygen generating system in fluid communication with the first inlet, a first fluid pathway, and a first outlet. The ventilator can include a second inlet to ambient air and a blower in fluid communication with the second inlet to draw ambient air. The ventilator can include a third inlet in fluid communication with the first fluid pathway upstream of the first outlet. The blower can also be in fluid communication with the second inlet to draw at least some of the extracted oxygen. The ventilator can also include a second outlet in fluid communication with the blower to dispense a mixture of the ambient air and the extracted oxygen to the user.

22 Claims, 9 Drawing Sheets

(51) Int. Cl.
*A61M 16/10* (2006.01)
*A61M 16/20* (2006.01)

(58) Field of Classification Search
CPC .............. A61M 16/122; A61M 16/125; A61M 2205/84; A62B 7/14
See application file for complete search history.

(56) References Cited

U.S. PATENT DOCUMENTS

| | | | |
|---|---|---|---|
| 4,883,051 A | 11/1989 | Westenskow et al. | |
| 7,225,809 B1 | 6/2007 | Bowen et al. | |
| 8,015,972 B2 | 9/2011 | Pirzada | |
| 8,096,783 B2 | 1/2012 | Grasmuck | |
| 8,734,097 B2 | 5/2014 | Kenyon et al. | |
| 9,616,188 B2 | 4/2017 | Grasmuck | |
| 10,328,228 B2 | 6/2019 | Zapol et al. | |
| 10,874,817 B1* | 12/2020 | Oddo | B01D 53/0454 |
| 11,517,702 B1* | 12/2022 | Wang | A61M 16/12 |
| 2002/0053286 A1* | 5/2002 | Czabala | A61M 16/101 95/130 |
| 2006/0144396 A1* | 7/2006 | DeVries | A61M 16/0057 128/204.26 |
| 2007/0125377 A1* | 6/2007 | Heinonen | A61M 16/204 128/204.21 |
| 2008/0156328 A1* | 7/2008 | Taube | A61M 16/122 128/204.22 |
| 2008/0202508 A1* | 8/2008 | McClain | A61M 16/101 128/201.21 |
| 2009/0133368 A1* | 5/2009 | Calkins | A61M 16/101 55/383 |
| 2009/0205661 A1* | 8/2009 | Stephenson | A61M 16/0051 128/205.24 |
| 2009/0291004 A1 | 11/2009 | Grasmuck | |
| 2010/0054969 A1 | 3/2010 | Grasmuck | |
| 2010/0189554 A1 | 7/2010 | Grasmuck | |
| 2011/0209707 A1* | 9/2011 | Terhark | B01D 53/0462 128/205.12 |
| 2012/0060841 A1* | 3/2012 | Crawford, Jr. | A61M 16/125 128/205.11 |
| 2013/0028710 A1 | 1/2013 | Kenyon et al. | |
| 2014/0014109 A1 | 1/2014 | Grasmuck | |
| 2014/0144433 A1* | 5/2014 | Martin | A61M 16/024 128/203.14 |
| 2014/0260991 A1* | 9/2014 | Null, Jr. | B01D 53/0415 96/147 |
| 2014/0283834 A1* | 9/2014 | Ahmad | A61M 16/0006 128/204.23 |
| 2015/0273174 A1* | 10/2015 | Hart | A61M 16/101 128/202.13 |
| 2017/0056613 A1* | 3/2017 | Cortez, Jr. | A61M 16/0672 |
| 2018/0001048 A1* | 1/2018 | Allum | A61M 16/106 |
| 2018/0110954 A1* | 4/2018 | Belisario | B01D 53/053 |
| 2018/0344963 A1* | 12/2018 | Taylor | B01D 53/047 |
| 2019/0099570 A1* | 4/2019 | Brambilla | A61M 16/0833 |
| 2019/0262572 A1* | 8/2019 | DeVries | A61M 16/0816 |
| 2019/0344033 A1* | 11/2019 | Ahmad | A61M 16/022 |
| 2020/0188624 A1* | 6/2020 | Nelson Mock | A61M 16/104 |
| 2020/0246566 A1* | 8/2020 | Sherman | A61M 16/101 |
| 2020/0261862 A1* | 8/2020 | Boulanger | B01F 23/191 |
| 2020/0368482 A1* | 11/2020 | Westfall | B01D 53/0407 |
| 2020/0405986 A1* | 12/2020 | Brambilla | A61M 16/0096 |
| 2021/0001075 A1* | 1/2021 | Oddo | B01D 53/0454 |
| 2021/0290889 A1* | 9/2021 | DeVries | A61M 16/208 |
| 2021/0299388 A1* | 9/2021 | Vankoevering | A61M 16/20 |
| 2022/0054791 A1* | 2/2022 | Cortez, Jr. | A61M 16/16 |
| 2022/0072250 A1* | 3/2022 | Kiljanek | A61M 16/0883 |
| 2022/0387745 A1* | 12/2022 | Cipollone | A61M 16/0057 |

FOREIGN PATENT DOCUMENTS

| | | | | |
|---|---|---|---|---|
| CN | 111973849 A | | 11/2020 | |
| CN | 112218674 A | | 1/2021 | |
| CN | 112938903 A | | 6/2021 | |
| EP | 3978057 A1 | * | 4/2022 | ........ A61M 16/0003 |
| GB | 2599239 A | * | 3/2022 | ............ A61M 16/12 |
| JP | 2011502547 A | | 1/2011 | |
| KR | 20060098347 A | | 9/2006 | |
| WO | WO-2013108172 A1 | * | 7/2013 | ......... B01D 53/0407 |
| WO | WO-2019202390 A1 | * | 10/2019 | ........... A61B 5/4836 |
| WO | WO-2021250582 A1 | * | 12/2021 | ........ A61M 16/0063 |

OTHER PUBLICATIONS

National Intellectual Property Administration PRC; Written Opinion of the International Search Authority for PCT/IB2022/055208 (common priority claim as the present application); Sep. 15, 2022; 4 pages.

China National Intellectual Property Administration; International Preliminary Report on Patentability; International Application PCT/IB2022/055208 (also claims priority to U.S. Appl. No. 63/211,237); Oct. 11, 2023.

Yu Ruyi; "Ventilator and Oxygen Concentrator—Can replace each other?"; web page; Feb. 6, 2020; single web page; no volume; publisher—Rokon Health; internet published at https://www.rokonhealth.com/ventilator-and-oxygen-concentrator-can-replace-each other/.

Alok Narkhede, Siddharth Gupta, Vivek Gorle, Aman Ninave, Tapesh Dule; "A Review on Portable Ventilator with Built in Oxygen Generator", web page; Jan. 2021; single web page; vol. 08, Issue 01; publisher—International Research Journal or Engineering and Technology (IRJET); internet published at https://www.irjet.net/archives/V8/i1/IRJET-V8I1304.pdf.

Patrick B. Murphy, PhD; Sunita Rehal, MSc; Gill Arbane, BSc (Hons); et al; Effect of Home Noninvasive Ventilation With Oxygen Therapy vs Oxygen Therapy Alone on Hospital Readmission or Death After an Acute COPD Exacerbation, web page; Jun. 6, 2017; single web page; vol. 317, No. 21; publisher—JAMA; internet published at https://jamanetwork.com/journals/jama/fullarticle/2627985?resultClick=1.

* cited by examiner

RESPIRATORY DEVICES

CROSS-REFERENCE TO RELATED APPLICATIONS

This application claims the benefit of U.S. Provisional Patent Application Ser. No. 63/211,237 for a RESPIRATORY DEVICES, filed on 2021 Jun. 16, which is hereby incorporated by reference in its entirety.

BACKGROUND

1. Field

The present disclosure relates to respiratory devices, such as oxygen concentrators and ventilators.

2. Description of Related Prior Art

In "A Review on Portable Ventilator with Built In Oxygen Generator" published in the International Research Journal of Engineering and Technology (IRJET)(Volume 08, Issue 01, pp 1830-3, https://www.irjet.net/archives/V8/i1/IRJET-V8I1304.pdf), the authors theorize a bag valve mechanism that will compress an Ambu bag which in turn will provide the necessary breathing to a patient, and also there is an electronic circuit that will control various parameters such as PEEP, tidal volume, breath per minute. In another part of the author's project is an oxygen generator and there are various methods to generate oxygen. The authors assert the most feasible and efficient method we found is by using a pressure swing adsorption process which uses pelletized Zeolite crystals as a separator.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A respiratory device can include an oxygen generator and a ventilator. The oxygen generator can include a first inlet to ambient air. The oxygen generator can include one of a vacuum swing oxygen generating system and a pressure swing oxygen generating system in fluid communication with the first inlet and thereby disposed to draw ambient air and extract oxygen from the ambient air. The oxygen generator can also include a first fluid pathway in fluid communication with the one of the vacuum swing oxygen generating system and the pressure swing oxygen generating system and thereby disposed to collect the extracted oxygen. The oxygen generator can also include a first outlet in fluid communication with the first fluid pathway and thereby disposed to dispense the extracted oxygen to a user. The ventilator can include a second inlet to ambient air. The ventilator can also include a blower in fluid communication with the second inlet and thereby disposed to draw ambient air. The ventilator can also include a third inlet in fluid communication with the first fluid pathway upstream of the first outlet. The blower can also be in fluid communication with the second inlet and thereby disposed to draw at least some of the extracted oxygen. The ventilator can also include a second outlet in fluid communication with the blower and thereby disposed to dispense a mixture of the ambient air and the extracted oxygen to the user.

BRIEF DESCRIPTION OF THE DRAWINGS

The detailed description set forth below references the following drawings.

DETAILED DESCRIPTION

Figure 1:
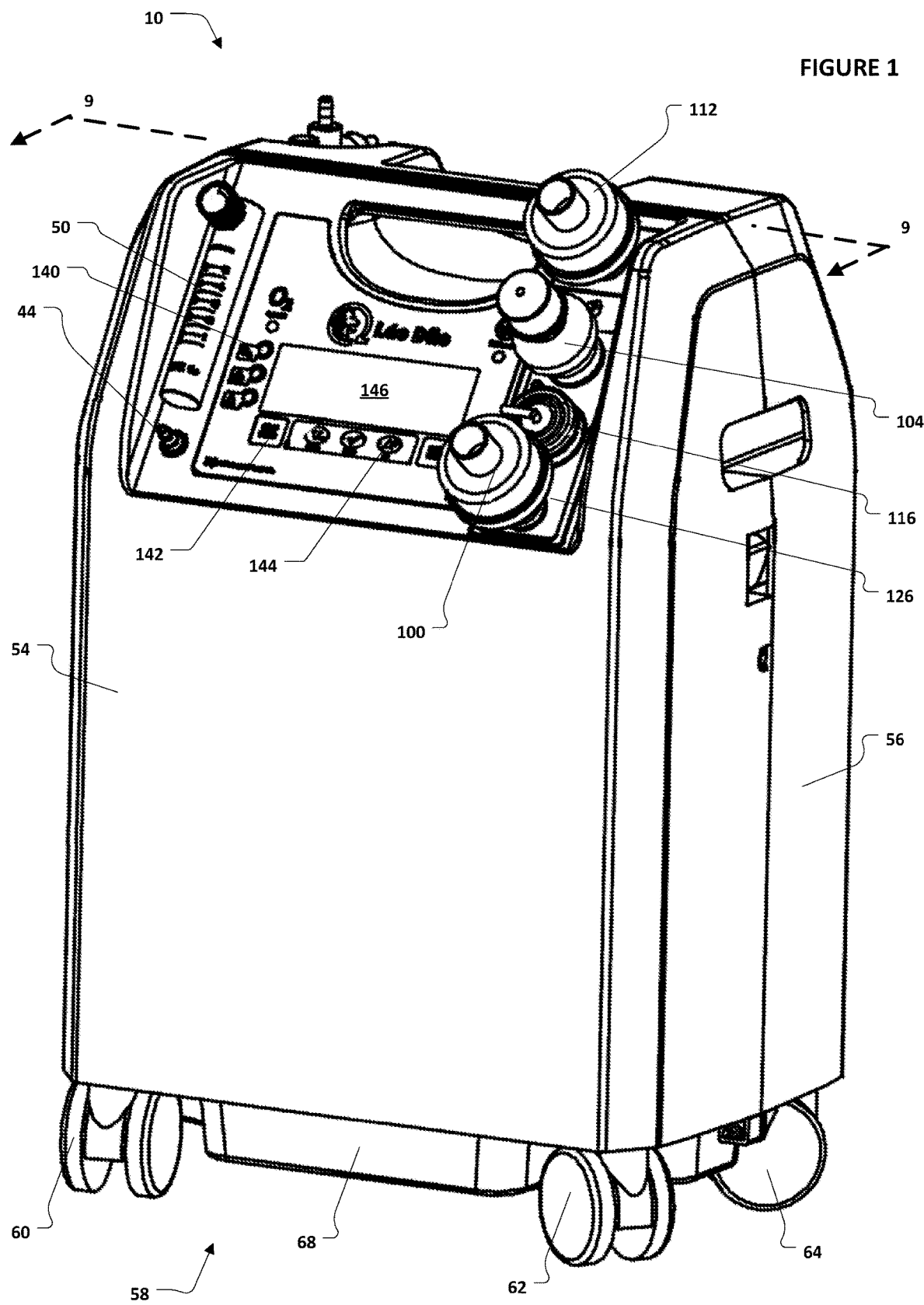
FIG. 1 is a first perspective view of a respiratory device according to an exemplary embodiment of the present disclosure.

The present disclosure, as demonstrated by the exemplary embodiment described below, can provide a respiratory device that incudes an oxygen generator and a ventilator. As shown in the Figures, a respiratory device 10 can include a housing having a first shell half 54 and second shell half 56. The respiratory device 10 can include a trolley 58 having a plurality of castor wheels 60, 62, 64, 66 and a carriage 68 resting on the plurality of wheels 60-66. The respiratory device 10 can also include an oxygen generator 12 and a ventilator 14. Both of the exemplary oxygen generator 12 and the exemplary ventilator 14 rest on the carriage 68 and can thus be jointly and easily moved as desired. Both of the exemplary oxygen generator 12 and the exemplary ventilator 14 are carried by the carriage 68.

Figure 3:
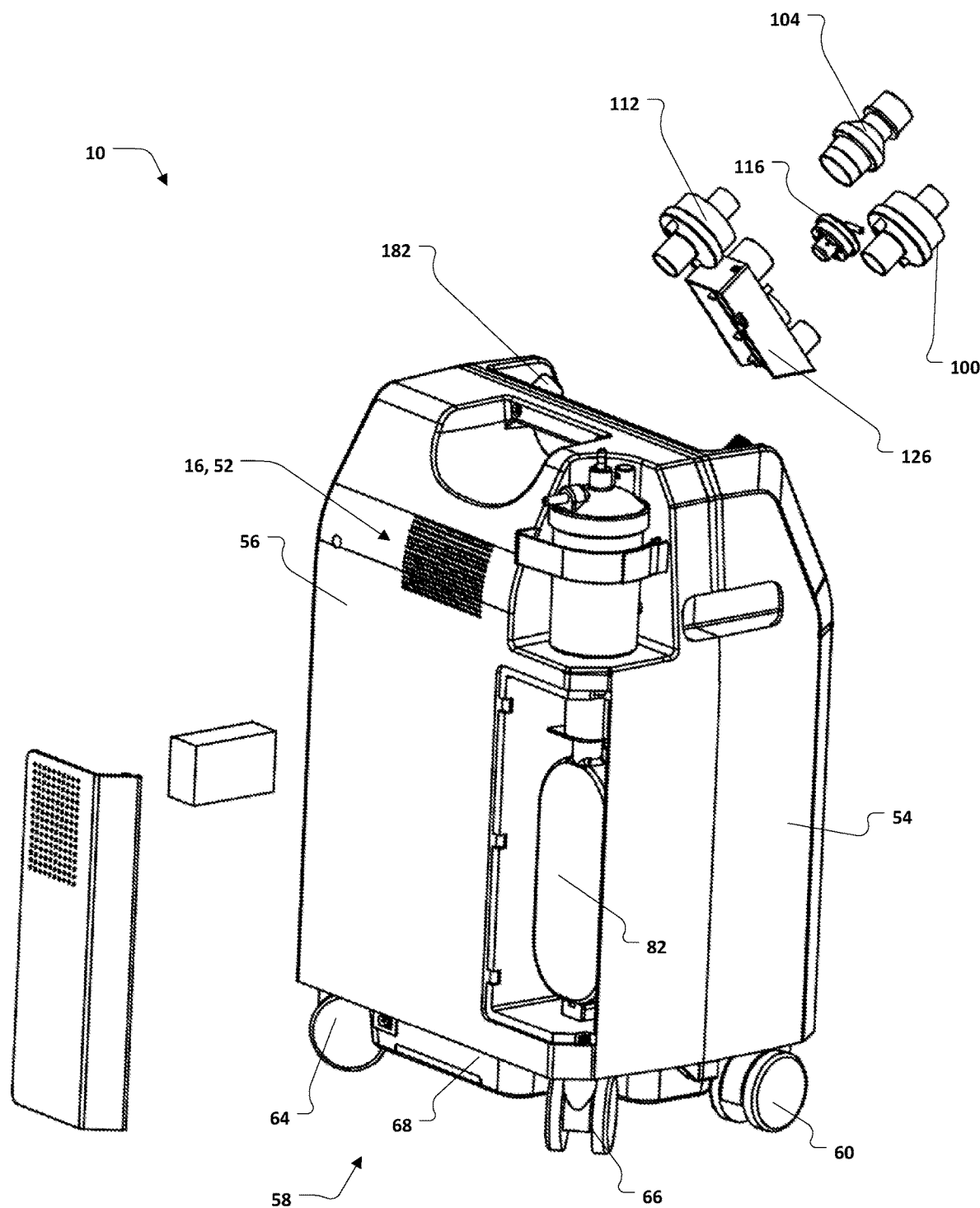
FIG. 3 is a second exploded view of the respiratory device shown in FIGS. 1 and 2.

The exemplary oxygen generator 12 can include an inlet 16 to ambient air. The exemplary inlet 16 (referenced in FIG. 3) is defined in the second shell half 56. The exemplary oxygen generator 12 can include one of a vacuum swing oxygen generating system and a pressure swing oxygen generating system. In the exemplary embodiment, the oxygen generator 12 is a pressure swing oxygen generating system 18.

Figure 2:
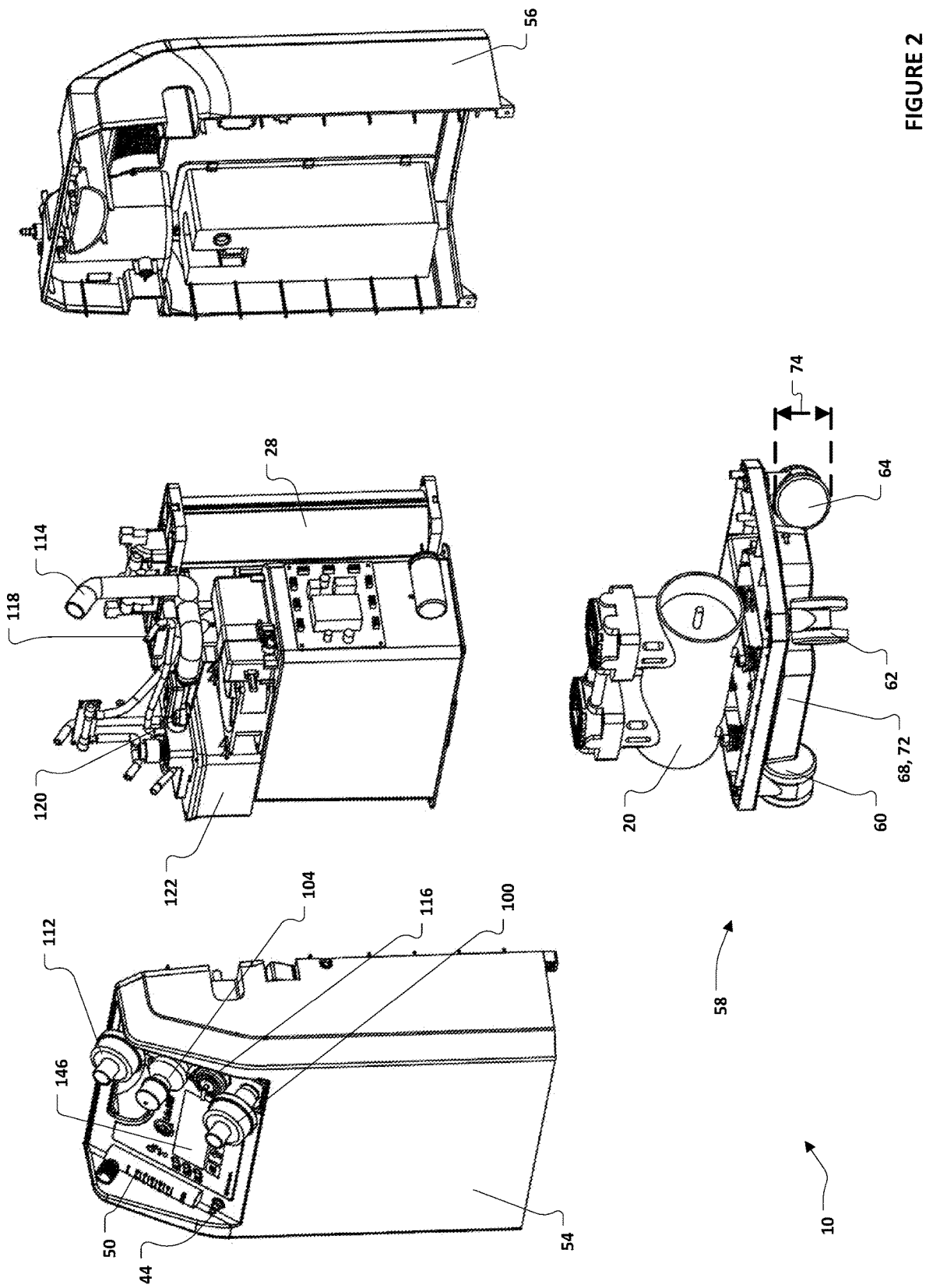
FIG. 2 is a first exploded view of the respiratory device shown in FIG. 1.

The exemplary pressure swing oxygen generating system 18 is in fluid communication with the inlet 16 and thereby disposed to draw ambient air. The exemplary pressure swing oxygen generating system 18 is configured extract oxygen from the ambient air. The exemplary pressure swing oxygen generating system 18 also includes a compressor 20 in fluid communication with the inlet 16 and thereby disposed to draw ambient air. The exemplary compressor 20 is configured to output compressed ambient air. In the exemplary embodiment, the compressor 20 draws ambient air through a cabinet filter 22 and a high-efficiency particulate air ("HEPA") filter 24. The compressor 20 rests in a well 72 defined by the carriage 68 and the well extends below a height 74 (referenced in FIG. 2) of the plurality of wheels 60-66. The castor wheels 60-66 are arranged around the well 72.

The exemplary pressure swing oxygen generating system 18 also includes a first sieve bed 28 holding a first quantity of zeolite. The exemplary first sieve bed 28 is in fluid communication with the compressor 20 to thereby receive the compressed ambient air. The exemplary pressure swing oxygen generating system 18 also includes a second sieve bed 30 holding a second quantity of zeolite. The exemplary second sieve bed 30 is also in fluid communication with the compressor 20 to thereby receive the compressed ambient air. The exemplary pressure swing oxygen generating system 18 also includes a muffler 32. The exemplary muffler 32 is in fluid communication with the first sieve bed 28 and the second sieve bed 30.

The exemplary pressure swing oxygen generating system 18 also includes a switching valve 34. The exemplary switching valve 34 interconnects the exemplary compressor 20 and the exemplary first sieve bed 28 and the exemplary second sieve bed 30 and the exemplary muffler 32. The exemplary switching valve 34 is configured to alternate between a first configuration and a second configuration. Compressed, ambient air is directed to the first sieve bed 28 when the exemplary switching valve 34 is in the first configuration. The exemplary second sieve bed 30 and the exemplary muffler 32 are placed in fluid communication with one another when the exemplary switching valve 34 is in the first configuration. Compressed, ambient air is directed to the second sieve bed 30 when the exemplary switching valve 34 is in the second configuration. The exemplary first sieve bed 28 and the exemplary muffler 32 are placed in fluid communication with one another when the switching valve 34 is in the second configuration.

The exemplary oxygen generator 12 includes a first fluid pathway 36 in fluid communication with the pressure swing oxygen generating system 18 and thereby disposed to collect the extracted oxygen. The exemplary first fluid pathway 36 includes fluid lines 38, 40. The exemplary pressure swing oxygen generating system 18 also includes a reservoir 42 in fluid communication with the first sieve bed 28 and with the second sieve bed 30 to thereby receive oxygen from the first sieve bed 28 and from the second sieve bed 30. The fluid line 38 extends between the first sieve bed 28 and the reservoir 42. The fluid line 40 extends between the second sieve bed 30 and the reservoir 42. The exemplary oxygen generator 12 also includes an outlet 44 in fluid communication with the first fluid pathway 36 and thereby disposed to dispense the extracted oxygen to a user.

In an exemplary method of operation, with the exemplary switching valve 34 in the first configuration, compressed air from the compressor 20 is directed into the first sieve bed 28. Nitrogen from the compressed ambient air is captured by the zeolite in the first sieve bed 28. Oxygen passes through the first sieve bed 28, through the fluid line 38, and into the reservoir 42. At the same time, nitrogen captured by the zeolite in the second sieve bed 30 releases from the zeolite and passes out of the muffler 32.

In another exemplary method of operation, with the exemplary switching valve 34 in the second configuration, compressed air from the compressor 20 is directed into the second sieve bed 30. Nitrogen from the compressed ambient air is captured by the zeolite in the second sieve bed 30. Oxygen passes through the second sieve bed 30, through the fluid line 40, and into the reservoir 42. At the same time, nitrogen captured by the zeolite in the first sieve bed 28 releases from the zeolite and passes out of the muffler 32.

The exemplary respiratory device 10 can also include a pressure regulator 46. The exemplary pressure regulator 46 is positioned downstream of the reservoir 44 along a fluid line 48 of the first fluid pathway 36. The exemplary pressure regulator 46 configured to regulate a pressure of the extracted oxygen to five-six pounds per square inch ("PSI"). A flowmeter 50 can also be disposed along the fluid line 48.

The exemplary ventilator 14 can include an inlet 52 to ambient air. It is noted that in the exemplary embodiment, the inlet 52 is the same as the inlet 16. The exemplary ventilator 14 can also include a blower 70 in fluid communication with the exemplary inlet 52 and thereby disposed to draw ambient air. In the exemplary embodiment, the blower 70 can draw ambient air through a HEPA filter 80.

The exemplary ventilator 14 also includes an inlet 76 in fluid communication with the first fluid pathway 36, upstream of the exemplary outlet 44. The exemplary blower 70 is in fluid communication with the inlet 76 and thereby disposed to draw at least some of the extracted oxygen. The respiratory device 10 includes a switching valve 78 interconnecting the inlet 76 and the first fluid pathway 36. The exemplary switching valve 78 is configured to alternate between a first configuration whereby extracted oxygen is directed to the outlet 44 and bypasses the inlet 76 and a second configuration whereby extracted oxygen is directed through the inlet 76 and bypasses the outlet 44. The switching valve 78 can be a solenoid valve, a manually-activated valve, or a proportional valve (a valve that switches in response to relative pressures in the connected fluid lines).

Figure 5:
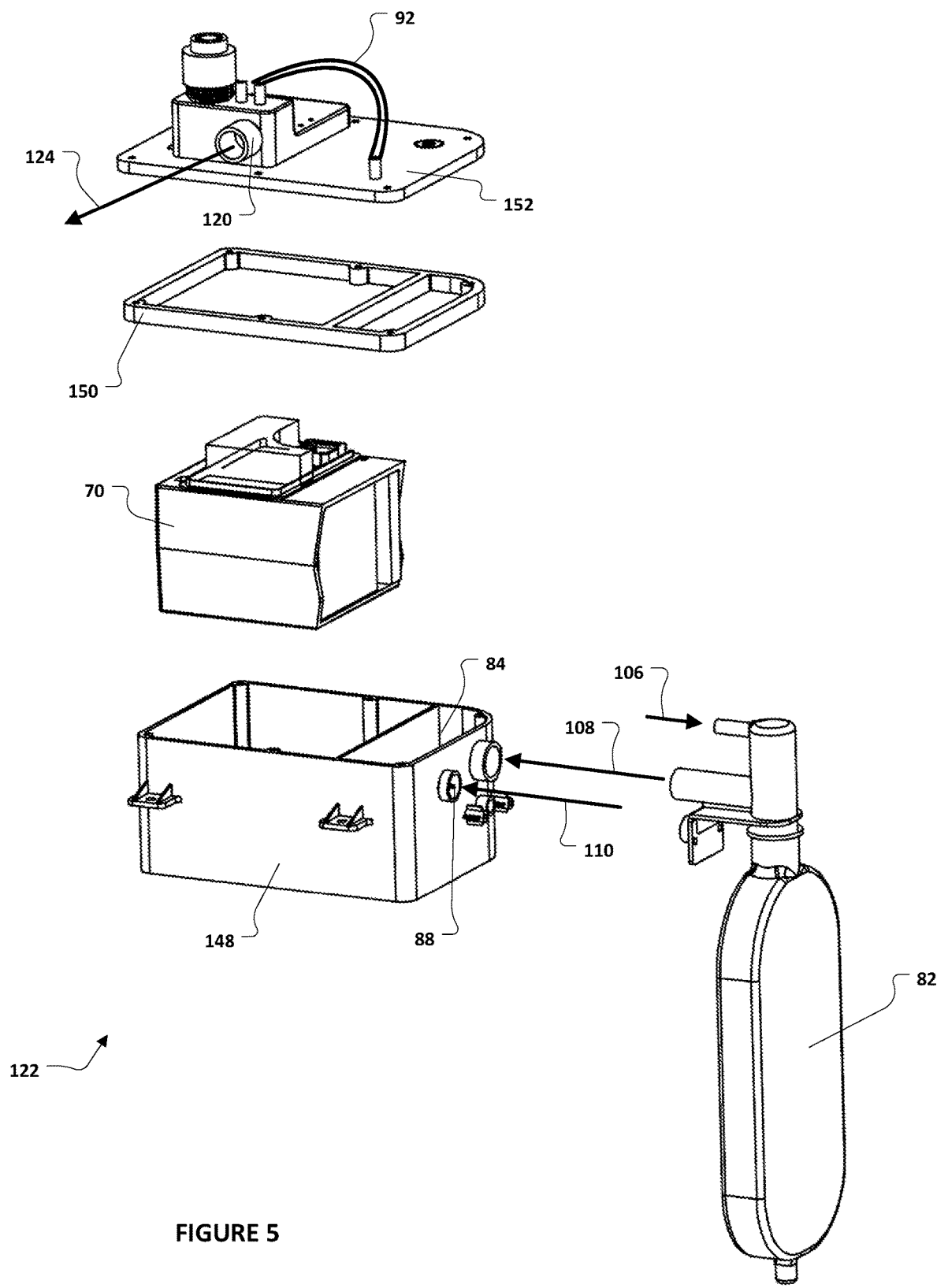
FIG. 5 is a third exploded view of part of the respiratory device shown in FIGS. 1-4.
Figure 6:
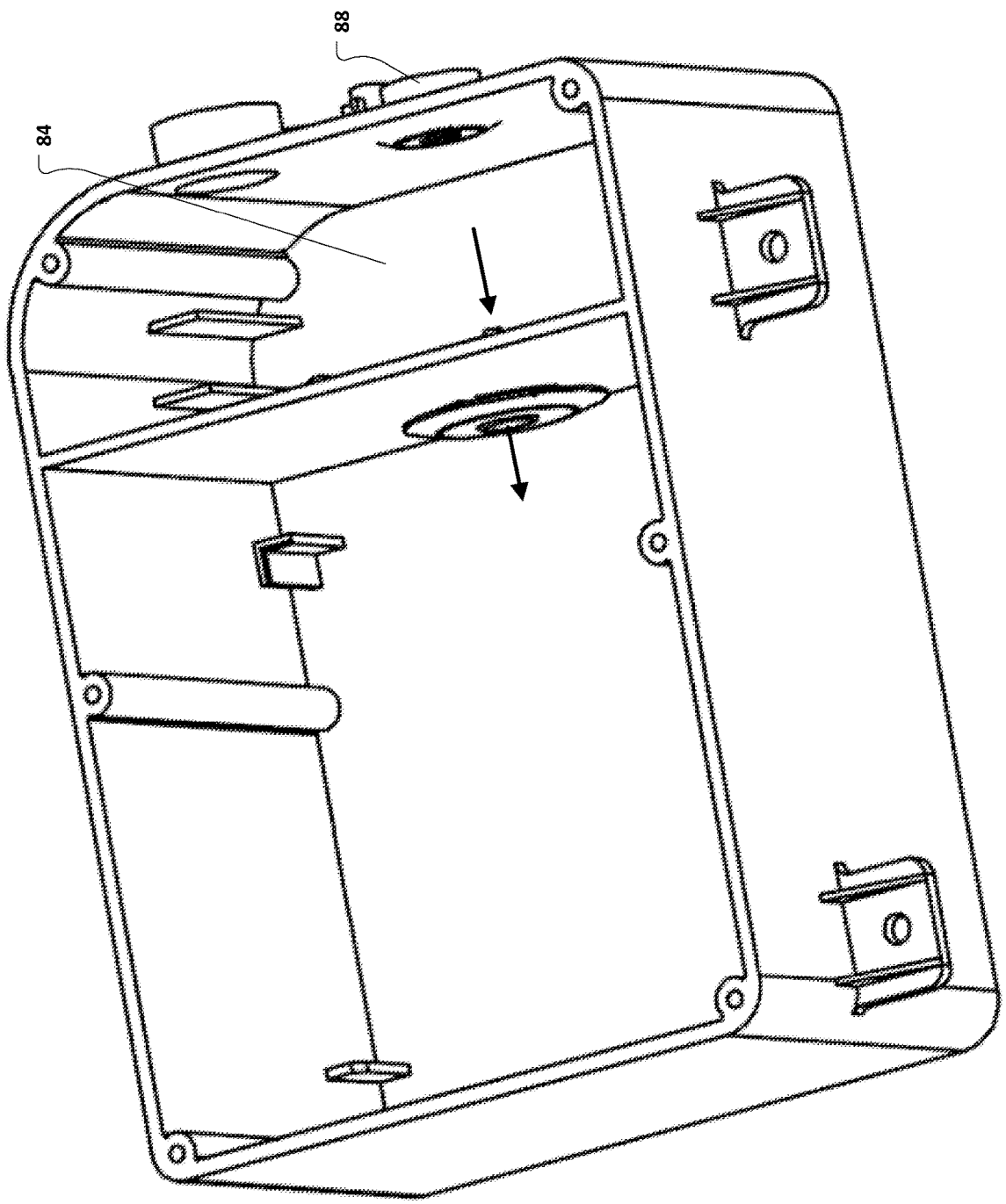
FIG. 6 is a third perspective view of a component of the respiratory device shown in FIGS. 1-5.

The exemplary respiratory device 10 also includes a reservoir 82 positioned downstream of the switching valve 78 and of the inlet 76. The reservoir 82 is disposed to retain extracted oxygen. In FIG. 5, the flow of oxygen into the reservoir 82 is referenced at 106 and the flow of oxygen out of the reservoir 82 is referenced at 108. The exemplary reservoir 82 is a self-inflating bag. A self-inflating bag is a bag that is elastically deformable. The self-inflating bag can be deformed from a static shape, such as collapsing in response to being subjected to the application of external pressure. When the application of external pressure ceases, the self-inflating bag can resume the static shape.

The exemplary ventilator 14 also includes a mixing chamber 84. The exemplary mixing chamber 84 is in fluid communication with the exemplary inlet 52 and also in fluid communication with the inlet 76. The exemplary mixing chamber 84 is downstream of the blower 70. The exemplary reservoir 82 is upstream of the mixing chamber 84. Ambient air drawn from the inlet 52 and oxygen drawn from the inlet 76 are mixed in the exemplary mixing chamber 84. In FIG. 5, the flow of oxygen into the mixing chamber 84 is referenced at 108 and the flow of ambient air into the mixing chamber 84 is referenced at 110.

The exemplary ventilator 14 can also include a pressure relief valve 86 in fluid communication with the mixing chamber 84. The exemplary pressure relief valve 86 can be rated one PSI. The exemplary ventilator 14 can also include a check valve 88 operably disposed between the inlet 52 and the mixing chamber 84 whereby movement of fluid in a direction from the mixing chamber 84 to the exemplary inlet 52 is prevented. The exemplary respiratory device 10 also includes a check valve 90 operably disposed between the blower 70 and the mixing chamber 84 whereby movement of fluid in a direction from the blower 70 to the exemplary inlet 52 is prevented. The exemplary respiratory device also includes a bleed line 92 extending in parallel to the check valve 90 and operably disposed between the blower 70 and the mixing chamber 84. The bleed line 92 inhibits spikes in pressure and also increases the amount of oxygen delivered to the patient.

Figure 7:
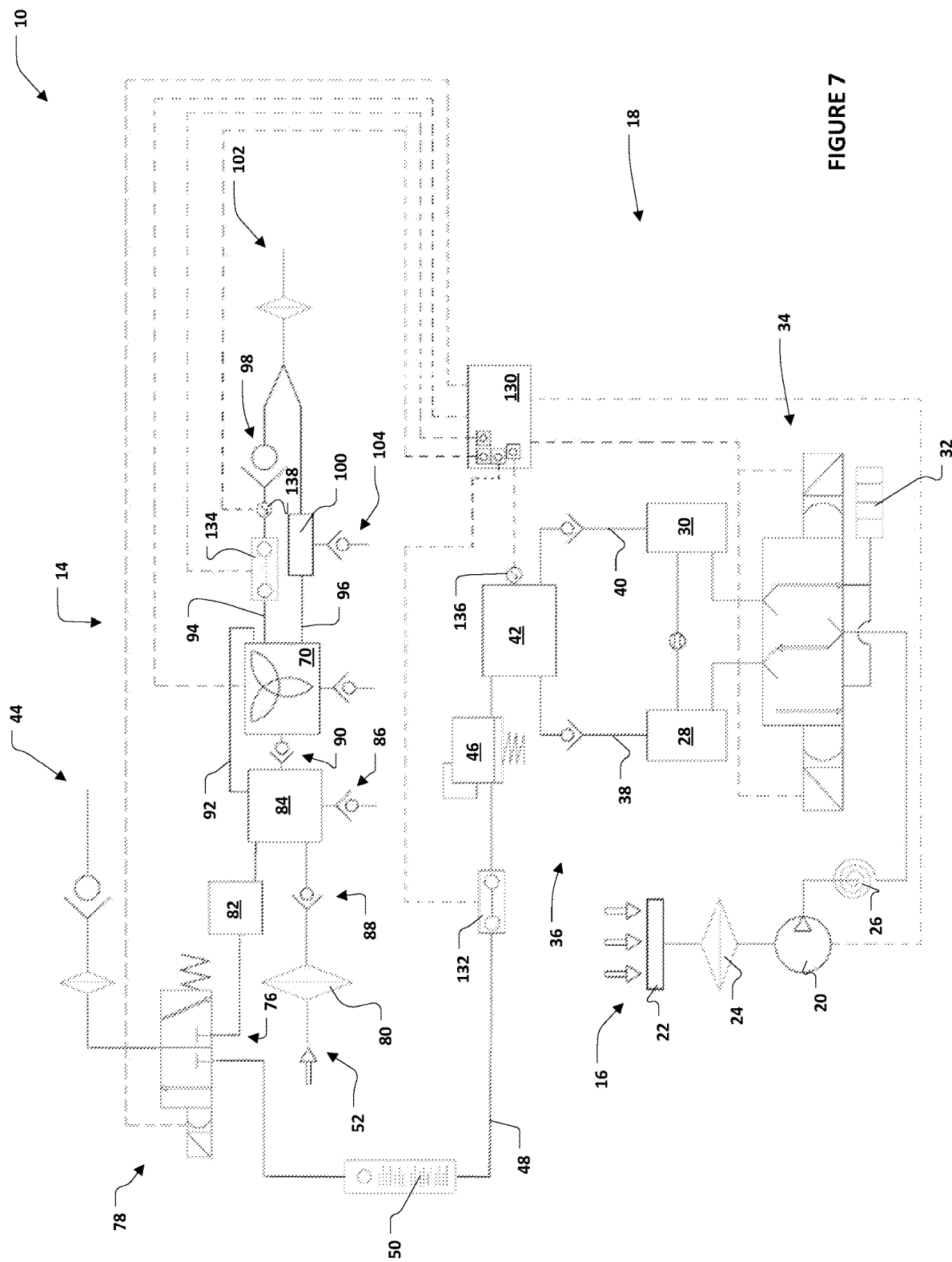
FIG. 7 is a schematic of the respiratory device shown in FIGS. 1-6.

Referring now to FIG. 7, the exemplary ventilator 14 can also include an outlet 102 in fluid communication with the blower 70 and thereby disposed to dispense a mixture of the ambient air and the extracted oxygen to the user. Referring now to the Figures generally, the exemplary ventilator 14 also includes an exhalation valve 100 mounted to a mounting block 126 that is mounted to the shell half 54. The exemplary exhalation valve 100 can be interconnected with a respiratory tube that extends to the user.

The exemplary exhalation valve 100 is a pressure-driven device. The exemplary exhalation valve 100 is connected to the blower 70 through a fluid line 96. When the blower 70 is running (during the inspiratory phase), the fluid pressure in fluid line 96 will cause the exemplary exhalation valve 100 to close. When the blower 70 is not running (during the expiratory phase), the exemplary exhalation valve 100 will be open and exhalation from the user will escape through the exemplary exhalation valve 100.

Figure 4:
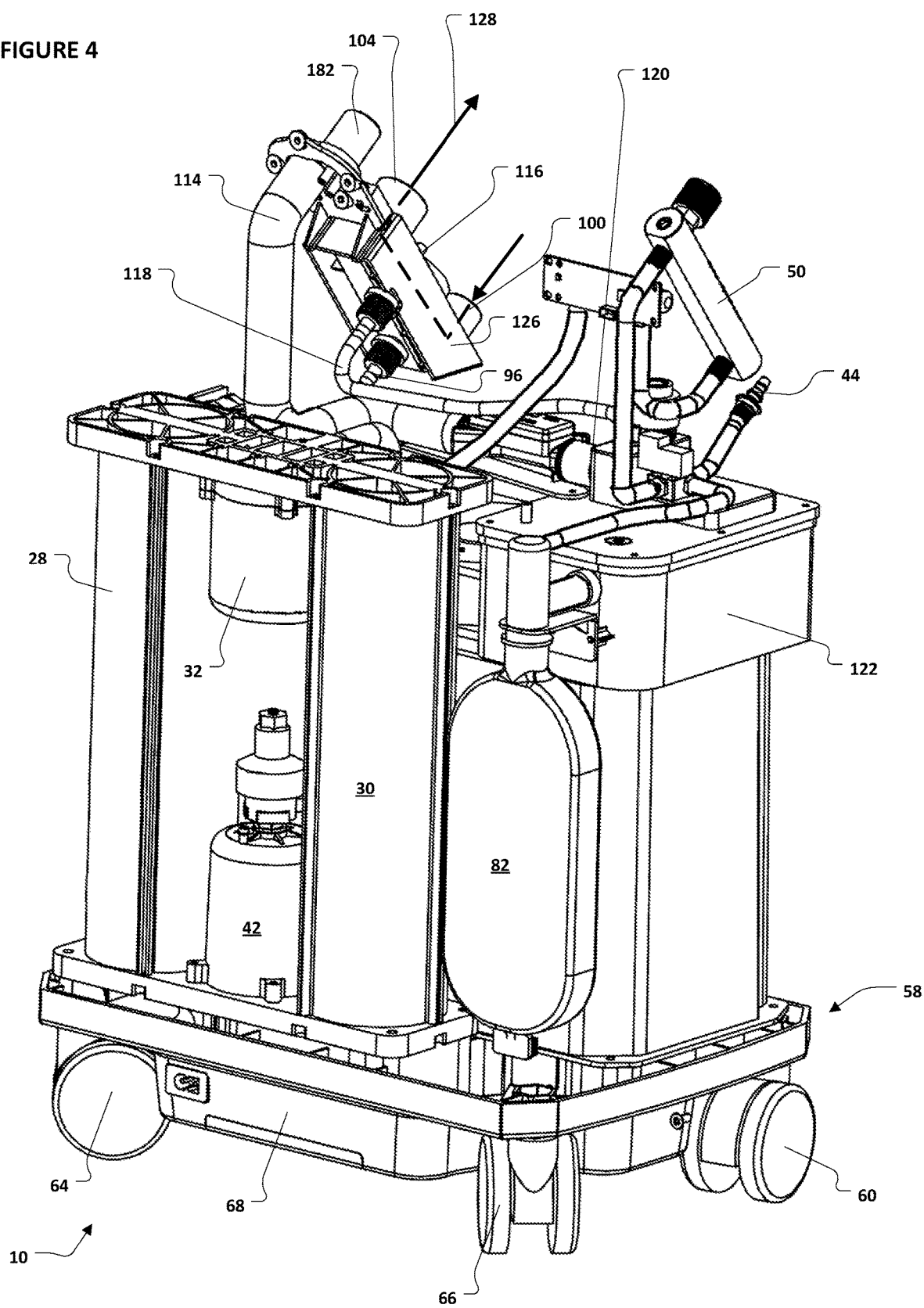
FIG. 4 is a second perspective view of part of the respiratory device shown in FIGS. 1-3.

The exemplary ventilator 14 also includes a positive end-expiratory pressure ("PEEP") valve 104. Exhalation will flow through the exemplary exhalation valve 100 and then through the PEEP valve 104 before reaching atmosphere. A flow of exhalation through the exhalation valve 100 and PEEP valve 104 is referenced at 128 in FIG. 4. The PEEP valve 104 is arranged to ensure that positive pressure that will remain in the airway communicating with the user at the end of the respiratory cycle (end of exhalation). A positive pressure is a pressure greater than the atmospheric pressure. The fluid pathway that extends between the exhalation valve 100 and the PEEP valve 104 can defined by the mounting block 126 that itself mounts into the shell half 54.

A fitting 112 can be mounted on the shell half 54. The fitting 112 can be fluidly connected to a fluid line 114 within the shell halves 54, 56. The fluid line 114 can extend to an outlet 120 of a blower housing assembly 122 in which the blower 70 is positioned. The exemplary assembly 122 includes a housing 148, the blower 70, a gasket 150, and a lid 152. Flow out of the outlet 120 is referenced at 124.

Flow from the fluid line 114 of the ventilator 14 can pass through the fitting 112 during the inspiratory phase. The fitting 112 can interconnect with a respiratory tube that extends to the user. A plurality of respiratory tubes can extend to the user, a first from the fitting 112 and a second from the exhalation valve 100. The respiratory tubes can be interconnected at the outlet 102. A check valve can be disposed in the respiratory tubing assembly so that exhalation is directed through the tube connected to the exhalation valve 100. An exemplary check valve that will prevent exhalation from flowing back to the blower 70 is referenced at 98 in FIG. 7.

The exemplary respiratory device 10 also includes a controller 130, sensors 132 and 134, and pressure sensors 136 and 138. The exemplary sensors 132 and 134 are oxygen and flow sensors. The exemplary sensors 132 and 134 can emit signals corresponding to the level of oxygen and the flow rate of the fluid moving in the fluid lines 48, 94 and the controller 130 can receive these signals. The exemplary sensors 136 and 138 can emit signals corresponding to the level of pressure of the fluid within the reservoir 42 and moving in the fluid line 94 and the controller 130 can receive these signals. The controller 130 can control the compressor 20 and the valves 34 and 78 in response the signals received from the sensors 132, 134, 136, 138.

The sensor 138 can be in fluid communication with a fitting 116 mounted in the mounting block 126 that is mounted on the shell half 54. A fluid line (not shown) can extend between the fitting 116 and the respiratory tube that extends to the user from the fitting 112. The fitting 116 can be fluidly connected to a fluid line 118 within the shell halves 54, 56. The sensor 138 can be disposed along the fluid line 118. It is noted that the fluid line 96 can branch off of the fluid line 118.

The exemplary controller 130 can also control and receive inputs from buttons and a touch display mounted in the shelf half 54. Exemplary buttons are referenced at 140, 142, 144 and an exemplary touch display is referenced at 146. A user of the exemplary respiratory device 10 can control the exemplary respiratory device 10 by inputting commands to the controller 130 through one or more of the buttons 140-144 and/or the display 146. For example, the user can control the exemplary respiratory device 10 to dispense oxygen through the output 44. Alternatively, the user can control the exemplary respiratory device 10 to operate the ventilator 14 to function as a continuous positive airway pressure ("CPAP") or as a bilevel positive airway pressure ("BiPAP").

Figure 8:
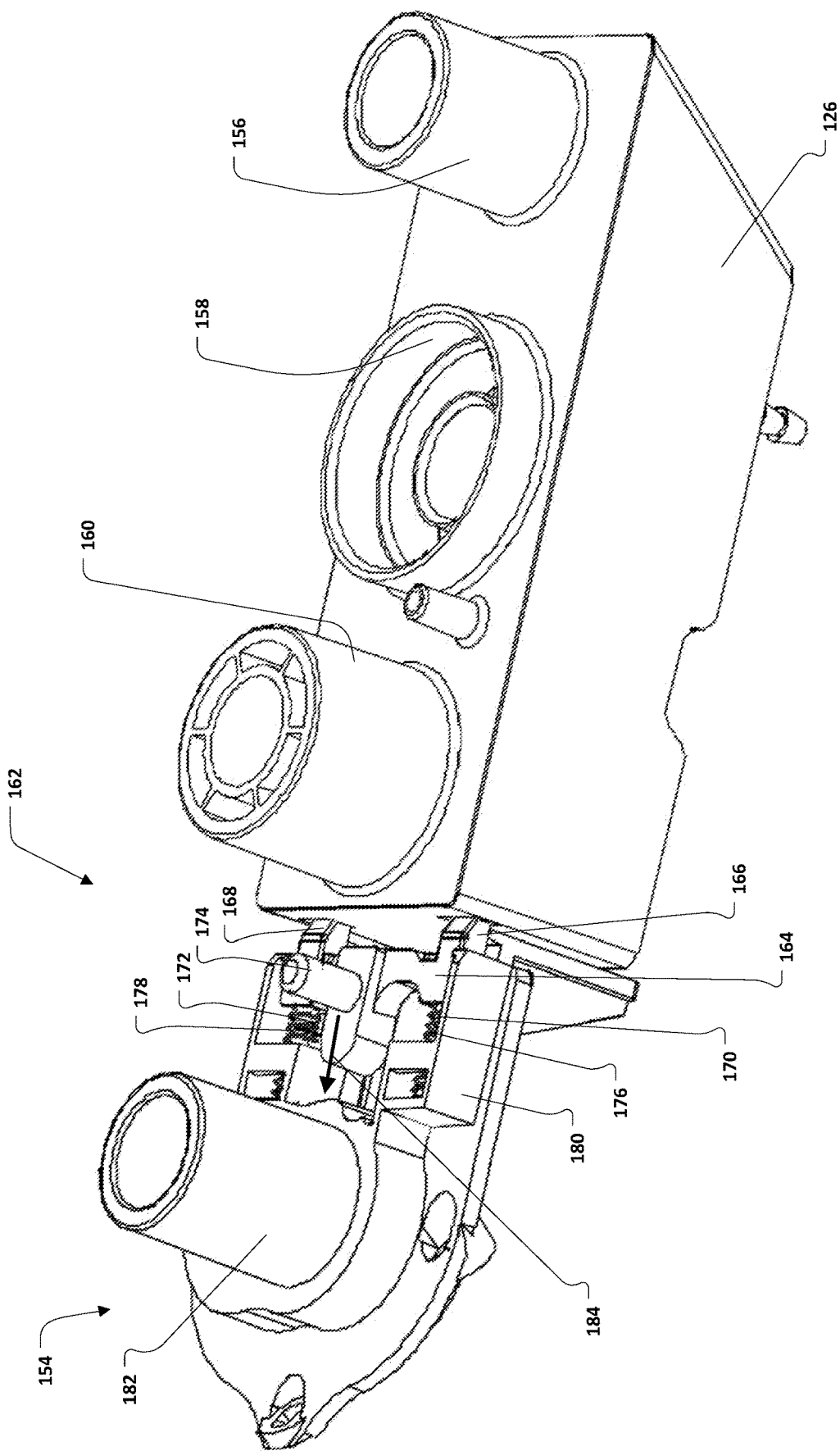
FIG. 8 is a perspective view of a mounting block of the respiratory device shown in FIGS. 1-7.
Figure 9:
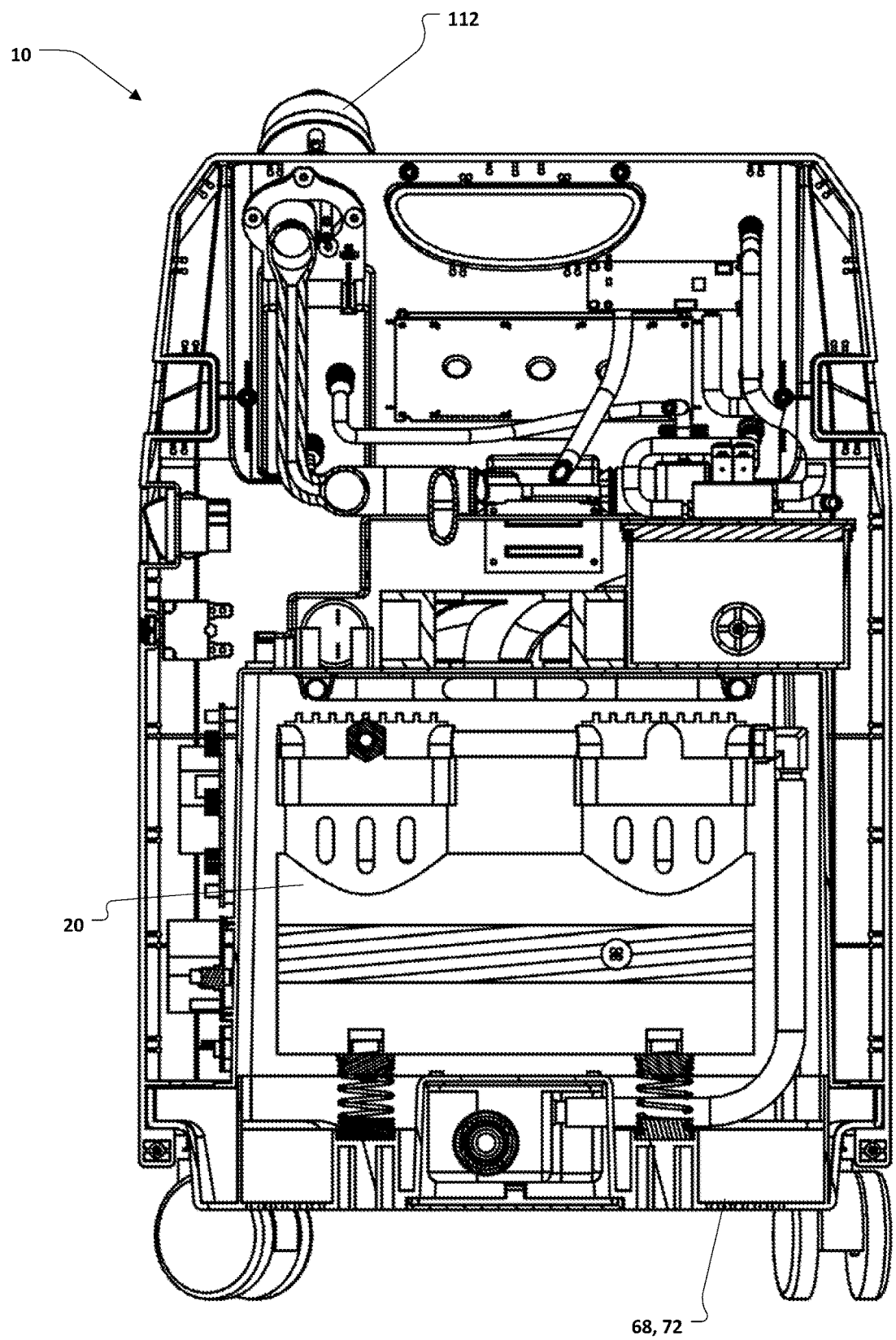
FIG. 9 is a cross-sectional view of the respiratory device shown in FIGS. 1-8 taken according to section lines 9-9 in FIG. 1.

Referring now to FIG. 8, the exemplary mounting block 126 can include posts 156, 158, 160. The exemplary exhalation valve 100 is mounted on the post 156. The exemplary PEEP valve 104 is mounted on the post 160. The exemplary fitting 116 is mounted on the post 158.

The exemplary respiratory device 10 also includes a mounting bracket 154. The exemplary mounting bracket 154 is fixed to the shell half 54. The exemplary fitting 112 can be mounted on a post 182 of the exemplary mounting bracket 154.

The exemplary shell half 54 includes an aperture sized and shaped to receive the exemplary mounting block 126. This aperture can be adjacent to the exemplary mounting bracket 154. The exemplary mounting block 126 is releasably attached to the exemplary mounting bracket 154 (and thus the shell half 54) with a spring-type slide and lock mechanism 162.

The exemplary spring-type slide and lock mechanism 162 includes a latch 164 having fingers 166, 168; guide posts 170, 172; and an actuating post 174. The exemplary spring-type slide and lock mechanism 162 also includes springs 176, 178. The spring 176 encircles the guide post 170 and the spring 178 encircles the guide post 172.

The exemplary latch 164 is received in a track 180 defined by the exemplary mounting bracket 154. The track 180 guides movement of the exemplary latch 164. When the exemplary mounting block 126 is being inserted into the aperture in the shell half 54, the actuating post 174 can be moved in the direction of the arrow referenced at 184. This will move the exemplary latch 164 against the biasing force generated by the springs 176, 178 and move the fingers 166,168 from interfering with insertion of the exemplary mounting block 126. When the exemplary mounting block 126 has been inserted into the aperture in the shell half 54, the actuating post 174 can be released. The springs 176, 178 will bias the latch 164 into movement in a direction opposite to the direction of arrow 184. The exemplary mounting block 126 can include apertures and the fingers 166, 168 can be inserted into these apertures as the latch 164 moves in the direction opposite to the direction of arrow 184. The fingers 166, 168 can lock the exemplary mounting block 126 in place, in the shell half 54.

While the present disclosure has been described with reference to an exemplary embodiment, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the appended claims. The right to claim elements and/or sub-combinations that are disclosed herein is hereby unconditionally reserved. The use of the word "can" in this document is not an assertion that the subject preceding the word is unimportant or unnecessary or "not critical" relative to anything else in this document. The word "can" is used herein in a positive and affirming sense and no other motive should be presumed. More than one "invention" may be disclosed in the present disclosure; an "invention" is defined by the content of a patent claim and not by the content of a detailed description of an embodiment of an invention.

What is claimed is:

1. A respiratory device comprising:
an oxygen generator having:
   a first inlet to ambient air,
   one of a vacuum swing oxygen generating system and a pressure swing oxygen generating system in fluid communication with said first inlet and thereby disposed to draw ambient air and extract oxygen from the ambient air,
   a first fluid pathway in fluid communication with said one of said vacuum swing oxygen generating system and said pressure swing oxygen generating system and thereby disposed to collect the extracted oxygen, and
   a first outlet in fluid communication with said first fluid pathway and thereby disposed to dispense the extracted oxygen to a user; and
a ventilator having:
   a second inlet to ambient air,
   a blower in fluid communication with said second inlet and thereby disposed to draw ambient air,
   a third inlet in fluid communication with said first fluid pathway upstream of said first outlet, wherein said blower is also in fluid communication with said third inlet and thereby disposed to draw at least some of the extracted oxygen, and
   a second outlet in fluid communication with said blower and thereby disposed to dispense a mixture of the ambient air and the extracted oxygen to the user.

2. The respiratory device of claim 1 further comprising:
a trolley having a plurality of wheels and a carriage resting on said plurality of wheels, wherein both of said oxygen generator and said ventilator rest on said carriage.

3. The respiratory device of claim 2 wherein:
said one of said vacuum swing oxygen generating system and said pressure swing oxygen generating system further comprises a compressor; and
said compressor rests in a well defined by said carriage and said well extends below a height of said plurality of wheels.

4. The respiratory device of claim 3 wherein said plurality of wheels are arranged around said well.

5. The respiratory device of claim 1 wherein said ventilator further comprises:

a mixing chamber in fluid communication with said second inlet and also in fluid communication with said third inlet, said mixing chamber downstream of said blower.

6. The respiratory device of claim 5 wherein said ventilator further comprises:
a first pressure relief valve in fluid communication with said mixing chamber.

7. The respiratory device of claim 5 wherein said respiratory device further comprises:
a first switching valve interconnecting said third inlet and said first fluid pathway, said first switching valve configured to alternate between a first configuration whereby extracted oxygen is directed to said first outlet and bypasses said third inlet and a second configuration whereby extracted oxygen is directed through said third inlet and bypasses said first outlet.

8. The respiratory device of claim 7 wherein said first switching valve is one of a solenoid valve and a manually-activated valve and a proportional valve.

9. The respiratory device of claim 7 wherein said respiratory device further comprises:
a first reservoir positioned downstream of said first switching valve and said third inlet and upstream of said mixing chamber, said first reservoir disposed to retain extracted oxygen.

10. The respiratory device of claim 9 wherein said first reservoir is further defined as a self-inflating bag.

11. The respiratory device of claim 9 further comprising:
a first check valve operably disposed between said second inlet and said mixing chamber whereby movement of fluid in a direction from said mixing chamber to said second inlet is prevented.

12. The respiratory device of claim 7 further comprising:
a second reservoir positioned upstream of said first switching valve along said first fluid pathway, said second reservoir disposed to retain extracted oxygen.

13. The respiratory device of claim 12 further comprising:
a pressure regulator positioned upstream of said first switching valve and downstream of said second reservoir along said first fluid pathway, said pressure regulator configured to regulate a pressure of the extracted oxygen.

14. The respiratory device of claim 5 further comprising:
a second check valve operably disposed between said blower and said mixing chamber whereby movement of fluid in a direction from said blower to said second inlet is prevented.

15. The respiratory device of claim 14 further comprising:
a bleed line extending in parallel to said second check valve and operably disposed between said blower and said mixing chamber.

16. The respiratory device of claim 1 wherein:
said one of said vacuum swing oxygen generating system and said pressure swing oxygen generating system is further defined as said pressure swing oxygen generating system and further comprises:
a fourth inlet to ambient air,
a compressor in fluid communication with said fourth inlet and thereby disposed to draw ambient air and configured to output compressed ambient air,
a first sieve bed holding a first quantity of zeolite and in fluid communication with said compressor to thereby receive the compressed ambient air,
a second sieve bed holding a second quantity of zeolite and in fluid communication with said compressor to thereby receive the compressed ambient air, a reservoir in fluid communication with said first sieve bed and with said second sieve bed to thereby receive oxygen from said first sieve bed and from said second sieve bed, a muffler, and a second switching valve interconnecting said compressor and said first sieve bed and said second sieve bed and said muffler, said second switching valve configured to alternate between a first configuration and a second configuration, wherein the compressed ambient air is directed to said first sieve bed when said second switching valve is in said first configuration, wherein said second sieve bed and said muffler are in fluid communication with one another when said second switching valve is in said first configuration, wherein the compressed ambient air is directed to said second sieve bed when said second switching valve is in said second configuration, wherein said first sieve bed and said muffler are in fluid communication with one another when said second switching valve is in said second configuration;

wherein said respiratory device further comprises a trolley having a plurality of wheels and a carriage resting on said plurality of wheels; and wherein both of said oxygen generator and said ventilator are carried by said carriage.

17. The respiratory device of claim 1 wherein said ventilator further comprises:

a first fluid line extending from said blower to said second outlet;

a second fluid line extending from said blower in parallel to said first fluid line; and an exhalation valve positioned between said second fluid line and said second outlet, said exhalation valve configured to be in a closed configuration when said blower is operating and be in an open configuration when said blower is not operating.

18. The respiratory device of claim 17 wherein said ventilator further comprises:

a positive end-expiratory pressure ("PEEP") valve in fluid communication with said exhalation valve wherein, when said exhalation valve is the open configuration, exhalation of the user flows from said second outlet, then through said exhalation valve, and then through said PEEP valve to atmosphere.

19. The respiratory device of claim 18 further comprising:

a mounting block, wherein said exhalation valve and said PEEP valve are both mounted in said mounting block.

20. The respiratory device of claim 19 wherein said mounting block defines a fluid passageway extending between said exhalation valve and said PEEP valve.

21. The respiratory device of claim 20 further comprising:

a sensor disposed to sense a pressure of fluid flow out of the ventilator; and a fitting mounted on said mounting block, said sensor in fluid in fluid communication with said fitting.

22. The respiratory device of claim 17 further comprising a mounting block that is attached to a remainder of said respiratory device with a spring-type slide and lock mechanism.

* * * * *